United States Patent [19]

Heath et al.

[11] 3,956,238

[45] *May 11, 1976

[54] POLYETHERQUINOXALINES

[75] Inventors: Darrell R. Heath, Overland Park, Kans.; Joseph G. Wirth, Schenectady, N.Y.

[73] Assignee: General Electric Company, Schenectady, N.Y.

[ * ] Notice: The portion of the term of this patent subsequent to Dec. 3, 1991, has been disclaimed.

[22] Filed: Aug. 26, 1974

[21] Appl. No.: 500,591

Related U.S. Application Data

[63] Continuation of Ser. No. 418,250, Nov. 23, 1973, Pat. No. 3,852,244.

[52] U.S. Cl. ................................ 260/47 R; 260/49; 260/50; 260/51.5; 260/65
[51] Int. Cl.² .......................................... C08G 73/06
[58] Field of Search ............ 260/50, 63 R, 65, 47 R, 260/49, 51.5, 52

[56] References Cited

UNITED STATES PATENTS

| 3,620,997 | 11/1971 | Marvel | 260/50 |
| 3,642,700 | 2/1972 | Augl | 260/50 |
| 3,654,226 | 4/1972 | Augl et al. | 260/50 |
| 3,661,850 | 5/1972 | Stille | 260/50 |
| 3,746,687 | 7/1973 | Duffy et al. | 260/50 |
| 3,792,017 | 2/1974 | Arnold et al. | 260/47 R |

*Primary Examiner*—Lester L. Lee
*Attorney, Agent, or Firm*—William A. Teoli; Joseph T. Cohen; Jerome C. Squillaro

[57] ABSTRACT

Polyetherquinoxalines are provided which are useful as injection molding compounds. The polyetherquinoxalines are the product of reaction of organic tetramine and bis(aromatic ether aromatic diketones).

7 Claims, No Drawings

POLYETHERQUINOXALINES

This is a continuation of application Ser. No. 418,250, filed Nov. 23, 1973, now U.S. Pat. No. 3,852,244.

The present invention relates to polyetherquinoxalines which are made by effecting reaction between organic tetramines and bis(aromatic ether aromatic diketones).

As shown in U.S. Pat. No. 3,730,946 of Heath, et al, assigned to the same assignee as the present invention, certain dinitro benzenoid compounds can be employed with alkali metal bisphenolates to make a variety of novel polymers. It has now been discovered that nitro-displacement of diketones of formula,

with alkali metal salts of dihydric phenols of the formula,

MOR$^1$OM, also can be employed to provide bis(aromatic ether aromatic diketones) of the formula, (I) 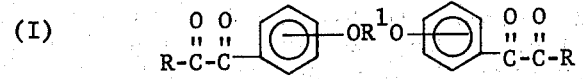

where R is a monovalent radical selected from hydrogen and a $C_{(1-13)}$ hydrocarbon and R$^1$ is a divalent aromatic radical having from 6–30 carbon atoms.

Radicals included by R are, for example, $C_{(1-8)}$ alkyl such as methyl, ethyl, propyl, butyl, pentyl, etc., aryl, such as phenyl, tolyl, xylyl, naphthyl, etc. Radicals included by R$^1$ are, for example, (a) the following divalent organic radicals:

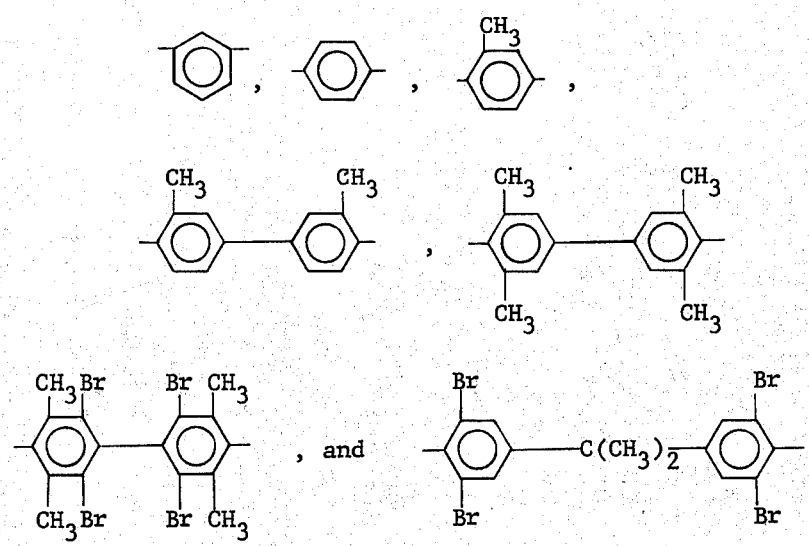

and (b) divalent organic radicals of the general formula

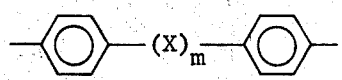

where X is a member selected from the class consisting of divalent radicals of the formulas, —$C_yH_{2y}$—,

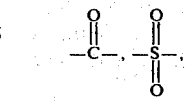

—O—, and —S—, where m is 0 or 1, and y is a whole number from 1 to 5.

The bis(aromatic ether aromatic diketones) of formula I, hereinafter referred to as the "tetra ketones" can be employed as plasticizers in a variety of organic resins such as polyvinylchloride, polyimides, polyurethanes, etc. In addition, the tetra ketones of the present invention can be reacted with tetramines of the formula,

(II)

where R$^2$ is a tetravalent $C_{(6-30)}$ aromatic organic radical defined below, to form polyetherquinoxalines having injection molding characteristics, consisting essentially of the following chemically combined units

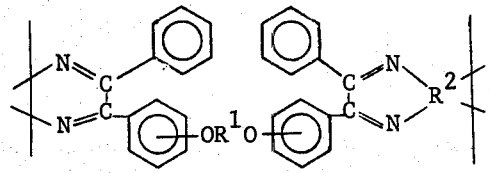

where R and R¹ are as previously defined.

Unlike the polyquinoxalines shown by Augl, et al, U.S. Pat. No. 3,654,226 and Stille, U.S. Pat. No. 3,661,850, the polyetherquinoxalines of the present invention have chemically combined aromatic ether linkages —ORO—, which render such materials injection moldable and soluble in relatively low polarity organic solvents such as chloroform and methylene chloride as well as the more polar solvents such as dimethylformamide, dimethylacetamide, etc.

There is provided by the present invention, moldable polymeric materials having recurring quinoxaline groups and an intrinsic viscosity in the range of from 0.1 to 2.0 which is the product of reaction of a tetra carbonyl compound of formula I and a tetramine of formula II in a non-oxidizing atmosphere and in the presence of a cresol solvent.

Radicals included by R² of formula II are, for example, tetra valent aromatic organic radical containing at least one ring of six carbon atoms, said rings characterized by benzenoid unsaturation, the four valence bonds being attached directly to separate carbon atoms, forming two respective pairs each of which are attached to adjacent carbon atoms on a ring, where said radicals are, for example,

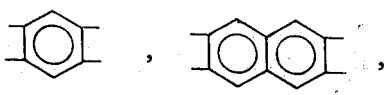

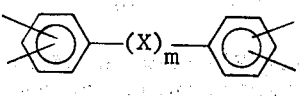

where X is a member selected from the class consisting of —$C_yH_{2y}$—, —O—,

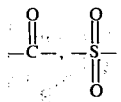

and —S—, where $m$ is 0 or 1, and $y$ is a whole number from 1 to 5.

Included by the tetra carbonyl compounds of formula I are, for example,

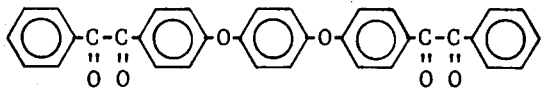

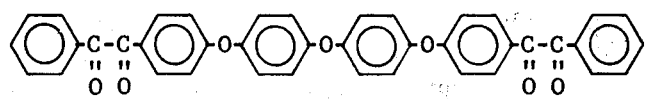

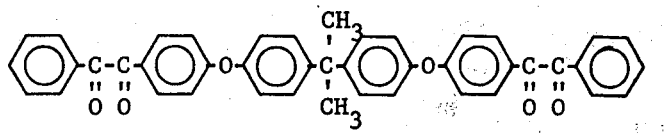

Included by the tetramine of formula II are, for example,

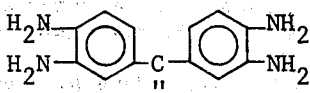

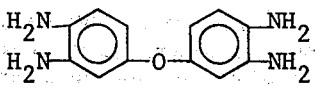

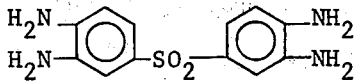

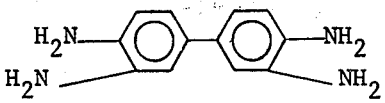

etc. Additional tetramines are shown in Stille, U.S. Pat. No. 3,661,850.

The alkali metal salts of the dihydric phenols which can be used to make the tetracarbonyl compounds of formula (I) by nitro-displacement are well known and include, for example, the disodium salt of 4,4'-dihydroxybiphenyl, the disodium salt of 4,4'-dihydroxydiphenyl sulfone, the dipotassium salt of 4,4'-dihydroxydiphenyl sulfide, etc. These alkali metal diphenoxides can be made by effecting reaction between an alkali metal hydroxide and a dihydric phenol. For example, the alkali metal salt of bisphenol-A can be obtained by reacting 2 moles of sodium hydroxide per mole of bisphenol-A. Again, alkali metal diphenoxides also can be made by adding 0.58 part of fresh cut of sodium metal to 75 parts of anhydrous methanol, with a magnetic stirrer under a nitrogen atmosphere. There is added to the mixture at the termination of the sodium reaction, 2.875 parts of bisphenol-A followed by evaporating the resulting solution to dryness. There is obtained a white solid upon drying the mixture further at 70°C.

Dihydric phenols which can be used to make the alkali metal salts of the dihydric phenols are, for example, 2,2-bis(2-hydroxyphenyl)propane;
2,4'-dihydroxydiphenylmethane;
bis(2-hydroxyphenyl)methane;
2,2-bis(4-hydroxyphenyl)propane, hereinafter identified as "bisphenol-A" or "BPA";
1,1-bis(4-hydroxyphenyl)ethane;
1,1-bis(4-hydroxyphenyl)propane;
2,2-bis(4-hydroxyphenyl)pentane;
3,3-bis(4-hydroxyphenyl)pentane;
4,4'-dihydroxybiphenyl;
4,4'-dihydroxy-3,3',5,5'-tetramethylbiphenyl;
2,4'-dihydroxybenzophenone;
4,4'-dihydroxydiphenyl sulfone;
2,4'-dihydroxydiphenyl sulfone;
4,4'-dihydroxydiphenyl sulfoxide;
4,4'-dihydroxydiphenyl sulfide;
hydroquinone;
resorcinol;
3,4'-dihydroxydiphenylmethane;
4,4'-dihydroxybenzophenone;
and 4,4'-dihydroxydiphenyl ether. In the practice of the invention, the tetramine and tetra carbonyl compound is contacted under a nitrogen atmosphere in the presence of a cresol solvent. The mixture is then poured into a precipitating solvent to recover polymeric product.

Optimum results are achieved when substantially equal moles of the tetramine and tetra carbonyl compound are employed, although there can be used from 0.8 to 1.2 moles of tetramine per mole of tetra carbonyl compound. Temperature of from 25° to 200°C can be employed with agitation of the reactants.

Cresol solvent which can be used can be o—, p—, or m-cresol, or a mixture thereof known as cresylic acid, as well as a mixture of such cresols and phenols. Reaction time can vary considerably and will depend upon such factors as degree of agitation, temperature, nature and proportion of reactants, etc. Accordingly from 0.5 to 20 hours will not be unusual. The crude polymeric product can be recovered by pouring the reaction mixture into an excess of precipitating solvent such as methanol, etc. The final polyetherquinoxaline can be reprecipitated by standard technique such as redissolving in chloroform and precipitating from methanol.

The polyetherquinoxalines of the present invention can be employed with carbon fibers to make composites reinforced with finely divided fillers such as silica gloss fibers, etc. in a proportion of from 50 to 200 parts of filler per 100 parts of polymer. The resulting reinforced polymers are injection moldable.

In order that those skilled in the art will be better able to practice the invention, the following examples are given by way of illustration and not by way of limitation. All parts are by weight.

EXAMPLE 1

A solution of 45.9 parts of 4-nitrobenzil and 16.74 parts of 4,4'-dihydroxybiphenyl and 202 parts of dimethylsulfoxide was stirred under nitrogen at 60°C with 62 parts of anhydrous potassium carbonate for 21 hours. The mixture was then carefully added with stirring to 2400 parts of 1N hydrochloric acid and 900 parts of chloroform. After one hour of stirring the layers were separated. The chloroform solution was extracted with six 300 part portions of 1N hydrochloric acid, dried with magnesium sulfate and stripped of solvent under reduced pressure. There was obtained 56.3 parts of a crude product which was recrystallized from 1000 parts of acetic acid. There was obtained 39.4 parts of a product having a melting point of 166°–168°C. Based on method of preparation, ¹H-NMR spectrum, ¹³C-NMR spectrum, mass spectrum, and elemental analysis, the product was a tetra carbonyl having the formula

Another recrystallization of benzene/cyclohexane resulted in a melting point of 167°–169°C.

There was added 2.8733 parts of the above tetracarbonyl compound along with 5 parts of cresol to a solution of 1.0216 parts of 3,3',4,4'-tetraminobiphenyl in 20 parts of cresol. The resulting mixture was stirred for 2.2 hours at a temperature of 95°–98°C. The mixture became homogeneous after a few minutes of heating while the viscosity gradually increased. The mixture was then refluxed for 15 minutes, cooled and added slowly to a large excess of methanol in a blender. There was obtained 3.51 parts of a precipitate which was dissolved in 75 parts of chloroform and reprecipitated from methanol. There was obtained 3.01 parts of product representing a yield of 85%, which had an intrinsic viscosity of 1.01 in chloroform. Based on method of preparation and elemental analysis the product was a polyetherquinoxaline consisting essentially of the following chemically combined units,

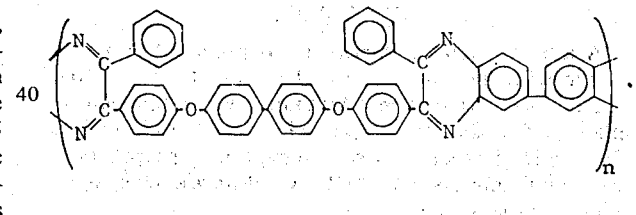

EXAMPLE 2

The procedure of Example 1 was repeated except in place of 3,3',4,4'-tetraminobiphenyl there was employed 3,3',4,4'-tetraminobenzophenone. There was obtained 3.61 parts representing a 96% yield of a polymeric reaction product having an intrinsic viscosity in chloroform at 25°C of 0.37. Based on method of preparation and elemental analysis, the product was a polyetherquinoxaline consisting essentially of the following chemically combined units,

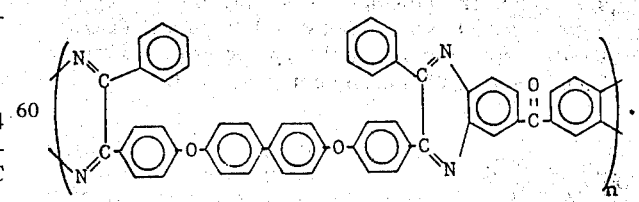

EXAMPLE 3

The procedure of Example 1 was repeated except that in place of 3,3',4,4'-tetraminobiphenyl, there was employed 3,3',4,4'-tetraminodiphenyl ether. There was obtained 3.86 parts which represented a 97% yield of a polymeric reaction product having an intrinsic viscosity in chloroform of 1.02. Based on method of preparation, $^{13}$C-NMR spectrum and elemental analysis, the product was a polyetherquinoxaline consisting essentially of the following chemically combined units,

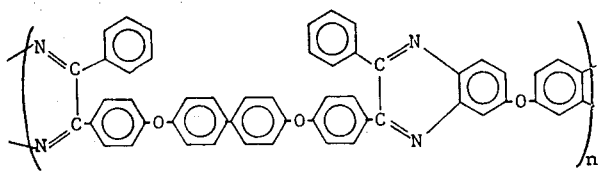

EXAMPLE 4

A polyetherquinoxaline was prepared in accordance with the procedure of Example 1, using 3,3',4,4'-tetraminodiphenyl sulfone in place of the tetramine of Example 1. There was obtained 3.48 parts which represented a 91% yield of a polymeric reaction product having an intrinsic viscosity of 0.19. Based on method of preparation and elemental analysis the product was a polyetherquinoxaline consisting essentially of the following chemically combined units,

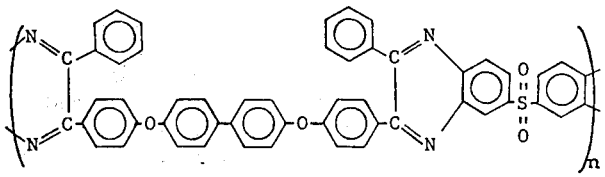

EXAMPLE 5

A tetra carbonyl compound was prepared in accordance with the procedure of Example 1, except that 2,2-bis-(4-hydroxyphenyl)methane was employed in place of 4,4'-dihydroxybiphenyl. There was obtained a 70% yield of product. Based on method of preparation, elemental analysis, $^1$H NMR, $^{13}$C NMR and mass spectra, the product was

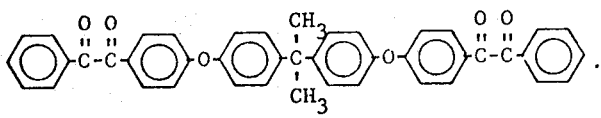

In accordance with the procedure of Example 1, equal moles of the above-described tetra carbonyl compound and tetraminobiphenyl ether was reacted in cresol. There was obtained a 74% yield of a polyetherquinoxaline. The polymer had an intrinsic viscosity in cresol of 0.17. Based on method of preparation and its $^{13}$C NMR spectrum, the polymer consisted essentially of the following chemically combined units,

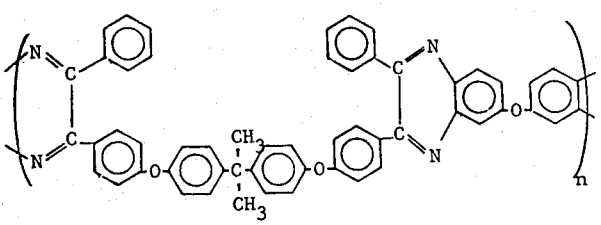

A hundred parts of the above polyetherquinoxaline is blended with 50 parts of fume silica. The blend is molded at 250°C for 5 minutes under a pressure of 4000 psi. A tough thermoplastic pellet is obtained.

Although the above examples are limited to only a few of the very many polyetherquinoxalines which can be made in accordance with the present invention, it should be understood that the present invention is directed to a much broader class of polyetherquinoxalines which can be made by effecting reaction between substantially equal moles of the tetra carbonyl compound of formula I and the tetramine of formula II.

What we claim as new and desire to secure by Letters Patent of the United States is:

1. Moldable polymeric materials having recurring quinoxaline groups and an intrinsic viscosity of from 0.1 to 2.0 in chloroform at 25°C consisting essentially of the following chemically combined units

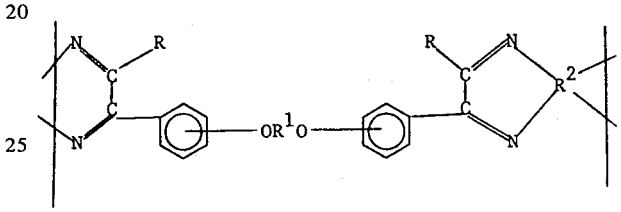

where R is a monovalent radical selected from hydrogen and a $C_{(1-13)}$ hydrocarbon, $R^1$ is a divalent aromatic radical having from 6–30 carbon atoms, and $R^2$ is a tetravalent aromatic organic radical.

2. A moldable polymeric material in accordance with claim 1, where the tetra carbonyl compound has the formula,

3. A moldable polymeric material in accordance with claim 1, where the tetra carbonyl compound has the formula

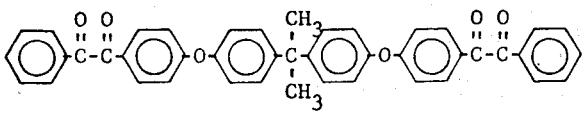

4. A moldable polymeric material in accordance with claim 1, where the tetramine is

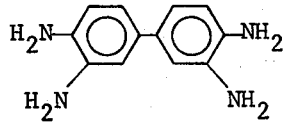

5. A moldable polymeric material in accordance with claim 1, where the tetramine is

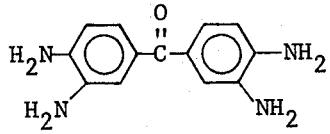

6. A moldable polymeric material in accordance with claim 1, where the tetramine is
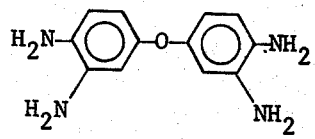
7. A moldable polymeric material in accordance with claim 1, where the tetramine is
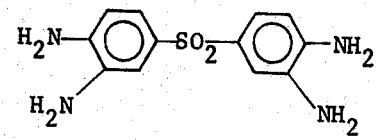
* * * * *